(12) United States Patent
Jacobi et al.

(10) Patent No.: US 8,491,911 B2
(45) Date of Patent: Jul. 23, 2013

(54) PHARMACEUTICAL PRODUCT FOR UP-DOSING OF ALLERGY VACCINE

(75) Inventors: Henrik Hugo Jacobi, Charlottenlund (DK); Eike Gunther Wüstenberg, Hamburg (DE); Lise Lund Mærkedahl, Fredensborg (DK)

(73) Assignee: Alk-Abello A/S, Horsholm (DK)

( * ) Notice: Subject to any disclaimer, the term of this patent is extended or adjusted under 35 U.S.C. 154(b) by 0 days.

(21) Appl. No.: 13/123,476

(22) PCT Filed: Oct. 15, 2009

(86) PCT No.: PCT/EP2009/063489
§ 371 (c)(1),
(2), (4) Date: Jun. 2, 2011

(87) PCT Pub. No.: WO2010/043675
PCT Pub. Date: Apr. 22, 2010

(65) Prior Publication Data
US 2011/0236426 A1 Sep. 29, 2011

(30) Foreign Application Priority Data

Oct. 15, 2008 (EP) .................................... 08166707
Oct. 17, 2008 (DK) ................................. 2008 01452
Dec. 22, 2008 (DK) ................................. 2008 01831
May 7, 2009 (DK) ................................. 2009 00587

(51) Int. Cl.
*A61K 39/00* (2006.01)
*A61K 39/38* (2006.01)
*A61K 39/35* (2006.01)
*A61K 39/36* (2006.01)

(52) U.S. Cl.
USPC .................................... 424/184.1; 424/275.1

(58) Field of Classification Search
None
See application file for complete search history.

(56) References Cited

U.S. PATENT DOCUMENTS

2005/0175638 A1* 8/2005 Esch .......................... 424/275.1
2006/0115499 A1* 6/2006 Brimnes et al. ............ 424/275.1

FOREIGN PATENT DOCUMENTS

WO WO-2008/116936 A1 10/2008

OTHER PUBLICATIONS

Jutel et al. 'Allergen-specific immunotherapy with recombinant grass pollen allergens.' J. Allergy Clin. Immunol. 116(3):608-613, 2005.*
Bauer et al., "Generation of hypoallergenic DNA vaccines by forced ubiquitination: Preventive and therapeutic effects in a mouse model of allergy," Journal of Allergy and Clinical Immunology, Mosby—Yearly Book, Inc., US, vol. 118, No. 1, Jul. 1, 2006, pp. 269-276.
Frew er al., "Efficacy and safety of specific immunotherapy with SQ allergen extract in treatment-resistant seasonal allergic rhinoconjuctivitis," Journal of Allergy and Clinical Immunology, Mosby—Yearly Book, Inc., US, vol. 117, No. 2, Feb. 1, 2006, pp. 319-325.
Alk-Scherax Arzneimittel GmbH: "ALK-depot SQ-Praparate," Gebrauchs- und Fachinformation, Apr. 2008.

* cited by examiner

*Primary Examiner* — Nora Rooney
(74) *Attorney, Agent, or Firm* — Birch, Stewart, Kolasch & Birch, LLP

(57) ABSTRACT

This invention relates to the use of a pharmaceutical product comprising allergen and optionally an adjuvant for fast up-dosing in connection with allergy vaccination wherein a reduced number of injections are used. The invention also relates to the pharmaceutical product as such.

26 Claims, No Drawings

PHARMACEUTICAL PRODUCT FOR UP-DOSING OF ALLERGY VACCINE

This application is the National Phase Under 35 U.S.C. §371 of PCT International Application No. PCT/EP2009/063489 which has an International filing date of Oct. 15, 2009, and which claims priority to European Patent Office Application No. 08166707.3 filed on Oct. 15, 2008; Application No. PA 2008 01452 filed in Denmark on Oct. 17, 2008; Application No. PA 2008 01831 filed in Denmark on Dec. 22, 2008; and Application No. PA 2009 00587 filed in Denmark on May 7, 2009. The entire contents of all applications listed above are hereby incorporated by reference.

This invention relates to the use of a pharmaceutical product comprising allergen and optionally an adjuvant for fast up-dosing in connection with allergy vaccination wherein a reduced number of injections are used. The invention also relates to the pharmaceutical product as such.

BACKGROUND OF THE INVENTION

Allergy is a major health problem in countries with a Western lifestyle. Furthermore, the prevalence of allergic disease is increasing in these countries. Although allergy in general may not be considered a life-threatening disease, asthma annually causes a significant number of deaths. An exceptional prevalence of about 30% of teenagers conveys a substantial loss in quality of life, working days and money, and warrants a classification among major health problems in the Western world.

Clinical allergy manifestation and symptoms are several and may vary depending on the sensitized individual and the allergy inflicted. Common are symptoms like edema, itching, redness and running of the eyes and nose (rhinitis and conjunctivitis) and symptoms from upper and lower airway like wheezing, coughing, shortness of breath, skin conditions like eczema, urticaria and itching. Other symptoms like fatigue are also experienced. Symptomatic treatment aims at reducing or affecting severity of the symptoms or reducing the need for other drugs given in parallel. Symptomatic drugs include antihistamines like $H_1$ and $H_2$ receptor antagonists, intranasal and systemic corticosteroids, non-steroid anti-inflammatory drugs, nasal decongestants like adrenoceptor agonists. Treatment and relief of one or more allergic symptom and/or the reduction in the need for other medication is a further object of this invention.

Symptomatic drugs are safe and efficient; however, they do not alter the natural cause of the disease, and they do not control the disease dissemination. A therapeutic alternative is specific allergy vaccination that in most cases reduces or alleviates the allergic symptoms caused by the allergen in question.

Conventional specific allergy vaccination (desensitization) is a causal treatment for allergic disease. It interferes with basic immunological mechanisms resulting in persistent improvement of the patients' immune status. Thus, the protective effect of specific allergy vaccination extends beyond the treatment period in contrast to symptomatic drug treatment. Some patients receiving the treatment are cured, and in addition, most patients experience a relief in disease severity and symptoms experienced, or at least an arrest in disease aggravation. Thus, specific allergy vaccination has preventive effects reducing the risk of hay fever developing into asthma, and reducing the risk of developing new sensitivities.

Conventional specific allergy vaccination or desensitisation is carried out using multiple subcutaneous immunizations with allergen (also called SCIT, SIT or subcutaneous immunotherapy) applied over an extended time period. The course is divided in two phases, the up dosing and the maintenance phase. In the up dosing phase increasing doses of allergen are applied, typically over a 16-week period, starting with minute doses. When the recommended maintenance dose is reached, this dose of allergen is applied for the maintenance phase, typically with injections every six weeks. Following each injection the patient must remain under medical attendance for 30 minutes due to the risk of anaphylactic side reactions, which in principle although extremely rare could be life-threatening. In addition, the clinic should be equipped to support emergency treatment.

As allergic individuals are an inhomogeneous group displaying different symptoms and different degrees of severity of their symptoms when exposed to even the same allergen, effective doses may vary. Some patients can tolerate larger doses without experiencing unacceptable side effects, while others are hypersensitive. In some cases escalating doses may be given to reach high dose levels as it is generally believed that larger doses are believed to be more effective doses.

Alutard SQ (Alk-Abello A/S) is a depot formulation in the form of a suspension for subcutaneous injection containing allergens adsorbed to aluminium hydroxide. Alutard SQ has been on the market for many years.

The maintenance dose for Alutard SQ depends on the individual patient and is suitable between 10.000 SQ-U and 100.000 SQ-U given every 4-8 weeks as a subcutaneous injection. To achieve optimal effect the maximal dose of 100.000 SQ-U should be used. However, maintenance doses as low as 10.000 SQ-U has been shown to have some effect, Frew A J, Powell R J, Corrigan C J, Durham S R. Efficacy and safety of specific immunotherapy with SQ allergen extract in treatment-resistant seasonal allergic rhinoconjunctivitis. J Allergy Clin Immunol 2006 February; 117 (2):319-25.

Up-dosing is conventionally carried out to avoid serious adverse effects by allowing patients to gradually become used to higher doses of the allergen.

For Alutard SQ up-dosing may be carried out as shown in table 1 below.

TABLE 1

| Vial No. | Concentration (SQ-U/ml) | Week No. | Injection No. | Volume (ml) | Dose (SQ-U) |
|---|---|---|---|---|---|
|   | 100 | 1 | 1 | 0.2 | 20 |
|   | 100 | 2 | 2 | 0.4 | 40 |
|   | 100 | 3 | 3 | 0.8 | 80 |
| 2 | 1.000 | 4 | 4 | 0.2 | 200 |
|   | 1.000 | 5 | 5 | 0.4 | 400 |
|   | 1.000 | 6 | 6 | 0.8 | 800 |
| 3 | 10.000 | 7 | 7 | 0.2 | 2.000 |
|   | 10.000 | 8 | 8 | 0.4 | 4.000 |
|   | 10.000 | 9 | 9 | 0.8 | 8.000 |
| 4 | 100.000 | 10 | 10 | 0.1 | 10.000 |
|   | 100.000 | 11 | 11 | 0.2 | 20.000 |
|   | 100.000 | 12 | 12 | 0.4 | 40.000 |
|   | 100.000 | 13 | 13 | 0.6 | 60.000 |
|   | 100.000 | 14 | 14 | 0.8 | 80.000 |
|   | 100.000 | 15 | 15 | 1.0 | 100.000 |

For Alutard SQ, the recommended interval between each incremental dose in the up-dosing phase is one week. However an interval of up to 14 days is allowed. If more than 14 days has passed since the previous dose, the previous dose is repeated or the dose is reduced.

An 8-step updosing schedule for Alutard SQ has been used for several years in the Scandinavian countries. This updosing schedule consists of 8 visits with one week intervals with 2-3 cluster injections during each visit. A maintenance dose of 100.000 SQ-U may thereby be reached in 8 weeks. The dose of 16.000 SQ-U may be reached after 3 visits and a total of 7 injections, Mellerup M T, Hahn G W, Poulsen L K, Mailing H. Safety of allergen-specific immunotherapy, Relation between dosage regimen, allergen extract, disease and systemic side-effects during induction treatment, Clin Exp Allergy 2000 October; 30 (10):1423-9.

Other products such as Pangramin Plus (ALK-Abello SpA) and ALK-7 (ALK-Scherax) allows a maintenance dose of 100.000 SQ-U to be reached in 7 weeks.

Recently it has been described that the maintenance dose in SIT can be reached via incremental doses given over a few consecutive days (ultra-rush SIT) and it is described how the maintenance dose of 100.000 SQ-U was reached on day 3 following subcutaneous injection of an increasing dose of birch allergen during 3 consecutive days, Månsson, A. el al, Ultra-rush specific immunotherapy against birch pollen-induced allergic rhinitis induces alterations in leukocyte phenotype, EAACHI, supplement 88, Volume 63, 2008, abstract 12.

It has now been found that the maintenance dose of a pharmaceutical product comprising allergen may be reached by an up-dosing schedule involving fewer injections. It has also been found that flexible time intervals between each incremental dose in the up-dosing phase may be used. The interval between each incremental dose may be as low as one day and as high as 14 days, which allow the patient to pick and chose the days for the injections in the up-dosing phase more freely than allowed by known up-dosing schedules. The number of injections to reach the maintenance dose may be as low as 5, 4, 3 or 2 injections.

It has also been found that a composition with a reduced dose of allergen (15.000 SQ-U as maintenance dose) compared to the Alutard SQ product may be very effective.

According to the invention the maintenance dose is typically 15.000 SQ-U suitably adsorbed to aluminium hydroxide in an amount corresponding to 0.5 to 0.6 mg aluminum ion, which means that the amount of injected aluminium hydroxide is reduced by 50% compared to the amount injected with a dose of 100.000 SQ-U of Alutard SQ.

The lower amount of aluminium hydroxide in compositions containing aluminium hydroxide as adjuvant will reduce adverse reactions at the injection site due to the aluminium hydroxide and the much lower amount of allergen administered with each injection will reduce the risk adverse reactions such as anaphylactic shock.

SUMMARY OF THE INVENTION

Accordingly the present invention relates to the use of a composition comprising allergen and optionally an adjuvant for the preparation of a pharmaceutical product for up-dosing in connection with allergy vaccination comprising one unit comprising a composition with one concentration of allergen or more separate units comprising a composition with different concentrations of allergen characterized in that the pharmaceutical product is provided in a form for administration of 2-10, preferably 2-6 subcutaneous injections containing an increasing amount of allergen and in that the intervals between the subcutaneous injections is flexible ranging from 1 to 14 days.

In a preferred embodiment the allergen is adsorbed to aluminiumhydroxide.

In another embodiment the pharmaceutical composition does not contain an adjuvant.

The invention also relates to the pharmaceutical product as such.

DETAILED DESCRIPTION OF THE INVENTION

The present invention is based on a number of surprising findings, none of which could with a reasonable expectation of success be predicted a priori.

First, it has been realized that up-dosing in connection with desensitization therapy with allergens may be carried out in a faster and more flexible manner compared to known up-dosing schedules.

Secondly, the invention is based on the finding that the amount of allergen in the maintenance dose may be reduced considerably.

Thirdly, the invention is based on the finding that it is also possible to reduce the amount of adjuvant such as aluminium hydroxide given with each injection.

According to one embodiment of the invention the pharmaceutical product comprises 1 to 6 units, preferably 1 to 5 units, more preferred 1 to 4 units, more preferred 1 to 3 units, even more preferred 2-3 units and most preferred 2 units containing the composition of the invention with different concentrations of allergen.

A "unit comprising or containing a composition of the invention" may be a vial, flask, ampoule or any other suitable container for a composition of the invention, which is normally in a liquid form, e.g. in the form of a suspension or a gel.

The increasing amount of allergen may be administered as different volumes of the same composition, or as the same volume of compositions with different concentration of allergen.

In one embodiment the pharmaceutical product for up-dosing is administered as 2 to 6, more preferred 2 to 5, more preferred 2 to 4, more preferred 2 to 3 and most preferred as 2 injections or 3 subcutaneous injections with increasing amount of allergen.

In another embodiment the pharmaceutical product for up-dosing is administered as 3 to 8, more preferred 4 to 7, more preferred 5 to 6 and most preferred as 5 subcutaneous injections with increasing amount of allergen.

In still another embodiment the pharmaceutical product is administered as 6 to 9, more preferred 7 to 8 and most preferred as 8 subcutaneous injections with increasing amount of allergen.

In another embodiment the pharmaceutical product for up-dosing is administered as 4, 5, 6 or 7 injections with increasing amount of allergen.

According to a further embodiment of the invention the interval between the subcutaneous injections is 3-14 days.

According to a further embodiment of the invention the interval between the subcutaneous injections is 3-4 days (bi-weekly) or 7 days (weekly).

According to a further embodiment of the invention the interval between the subcutaneous injections is 1 to 7 days, more preferred 1 to 6 days, more preferred 1 to 4 days, more preferred 1 to 3 days, more preferred 1 to 2 days and most preferred 1 day.

In one preferred embodiment the interval between injections in the up-dosing phase is 7 days or once a week. Preferably, the op-dosing consist of 5 injections with 7 days or one week between the injections (i.e. 4 weeks to reach the maintenance dose).

In one preferred embodiment, the up-dosing consist of 5 injections with 7 days or one week between the injections and the allergen is a grass allergen.

The pharmaceutical product of the invention may also comprise one or more units comprising the composition to be used in the maintenance phase.

The maintenance dose corresponds to the last and highest dose in the up-dosing phase.

According to the invention the pharmaceutical composition is preferably administered by subcutaneous injections. However, the pharmaceutical composition of the invention could also be administered via the intracutaneous route.

As used herein the term "allergen" refers to any naturally occurring protein or mixtures of proteins that have been reported to induce allergic, i.e. IgE mediated reactions upon their repeated exposure to an individual. Examples of naturally occurring allergens include pollen allergens (tree, weed, herb and grass pollen allergens), mite allergens (from e.g. house dust mites and storage mites), insect allergens (inhalant, saliva- and venom origin allergens), animal allergens from e.g. saliva, hair and dander from e.g. dog, cat, horse, rat, mouse, etc., fungi allergens and food allergens. The allergen may be used in the form of an allergen extract, a purified allergen, a modified allergen (e.g. allergoids) or a recombinant allergen or a recombinant mutant allergen, any allergen fragment above 30 amino acids or any combination thereof.

In one embodiment of the invention the allergen is not an irreversibly chemically modified allergen, such as allergoid(s) which are typically allergen(s) (e.g. allergen extracts) chemically modified by reaction with glutaraldehyde or formaldehyde).

The expression "allergen extract" as used therein refers to an extract obtained by extraction of a biological allergen source material as generally described in "Allergenic extracts", H. Ipsen et al, chapter 20 in Allergy, principle and practise (Ed. S. Manning) 1993, Mosby-Year Book, St. Louis. Such extracts may be obtained by aqueous extraction of water soluble material followed by purification steps like filtration to obtain the solution i.e. the extract. The extract may then be subjected to further purification and/or processing like freeze-drying removing substantially all the water. Generally, an allergen extract comprises a mixture of proteins and other molecules. Allergen proteins are often classified as a major allergen, an intermediate allergen, a minor allergen or no classification. An allergen extract generally comprises both major and minor allergens. Major allergens will generally constitute approximately 5-15% of an average allergen extract, more often about 10%. The average allergic person will be sensitised to and react to one or more major allergens and further may also be sensitized and react to minor allergens.

Amounts of allergen extract referred to herein refers to the dry matter content of such allergen extracts.

Preferably the water content of the dry matter does not exceed 10%, more preferably 5% by weight.

Normally at least 10% of the dry matter content of an allergen extract is protein as determined in a standard protein assay such as BCA or Lowry and the remainder consists of other "non-protein material," which may be components such as lipids, carbohydrates, or bound water which originate from the biological allergen source.

An allergen extract may be formulated and stored in form of a freeze-dried material obtainable by freeze-drying a liquid allergen extract at a pressure of below 800 micro bar and for a period of up till 100 hours removing the water.

In the field of allergy extracts, there is no international accepted standardization method. A number of different units of extract strength i.e. bio-potency exist. The methods employed and the units used normally measure the allergen content and biological activity. Examples hereof are SQ-Units (Standardized Quality units), BAU (Biological Allergen Units), BU (biological units), UM (Units of Mass), IU (International Units) and IR (Index of Reactivity). Hence, if extracts of origins other than those disclosed herein are used, they need to be standardised against extract disclosed herein in order to determine their potency in SQ units or any of the above mentioned units. The subject matter is dealt with in "Allergenic extracts", H. Ipsen et al, chapter 20 in Allergy, principle and practise (Ed. S. Manning) 1993, Mosby-Year Book, St. Louis and Løwenstein H. (1980) Arb Paul Ehrlich Inst 75:122.

The bio-potency, i.e. the in vivo allergenic activity, of a given extract depends on a number of factors, the most important being the content of major allergens in the extract, which varies with the composition of the biological source material.

The amount of allergen extract in grams to be used for obtaining a desired bio-potency varies with the type of extract in question, and for a given type of extract the amount of allergen extract varies from one batch to another with the actual bio-potency of the extract.

For a given batch of extract, the amount of allergen extract in grams to be used for obtaining a desired bio-potency may be determined using the following procedure:

a) The bio-potency of various amounts of a reference extract is determined using one or more immunological in vivo tests to establish a relationship between bio-potency and amount of reference extract. Examples of the said immunological in vivo tests are Skin Prick Test (SPT), Conjunctival Provocation Test (CPT), Bronchial Challenge with Allergen (BCA) and various clinical trials in which one or more allergy symptoms is monitored, see for example e.g. Haugaard et al., J Allergy Clin Immunol, Vol. 91, No. 3, pp 709-722, March 1993.

b) On the basis of the established relationship between bio-potency and reference extract, the bio-potency of one or more relevant doses for use in the dosage forms is selected with due consideration to a balance of the factors of i) the effect of treating or alleviating symptoms of allergy, ii) side effects recorded in the immunological in vivo tests, and iii) the variability of i) and ii) from one individual to another. The balancing is done to obtain a maximal adequate therapeutic effect without experiencing an unacceptable level of side effect. The way of balancing the factors are well known to those skilled in the art The bio-potency of the one or more relevant doses found may be expressed in any biopotency unit available, such as SQ units, BAU, IR units, IU, cf. above.

c) From the reference extract one or more bio-potency reference standard extracts is prepared and, if used, the bio-potency unit values of the reference standard extracts are calculated on the basis of the bio-potency unit value allocated to the one or more relevant doses, e.g. such a standard for BAU can be obtained from FDA as illustrated below.

d) For the reference standard extracts of each extract type, a number of parameters for evaluating the bio-potency of extracts are selected. Examples of such evaluation parameters are total allergenic activity, the amount of defined major allergens and overall molecular composition of the extract. The total allergenic activity may be measured using an in vitro competitive immunoassay, such as ELISA and MagicLite® luminescence immunoassay (LIA), using a standardised antibody mixture raised against the extract obtained using standard methods, e.g. antibodies raised in mouse or rabbit, or a pool of allergic patients sera. The content of major allergens may e.g. be quantified by, Elisa, MS-quantification as described in PCT/DK2006/000480 or rocket immunoelectrophoresis (RIE) and compared to the reference standards. The overall molecular composition may be examined using e.g. crossed immunoelectrophoresis (CIE) and sodium dodecyl sulphate polyacrylamide gel electrophoresis (SDS-PAGE).

e) For a given batch of extract of unknown bio-potency (test extract), the amount of extract to be used for obtaining a desired bio-potency level (effective) may be determined as follows: For each evaluation parameter selected, the test extract is compared with the reference standard extracts using the relevant measurement methods as described above, and on the basis of the measurement results the amount of extract having the desired bio-potency is calculated.

SQ-Unit: The SQ-Unit is determined in accordance with ALK-Abelló A/S's "SQ biopoticity"-standardisation method, where 100,000 SQ units equal the standard subcutaneous maintenance dose. Normally 1 mg of extract contains between 100,000 and 1,000,000 SQ-Units, depending on the allergen source from which they originate and the manufacturing process used. The precise allergen amount can be determined by means of immunoassay i.e. total major allergen content and total allergen activity.

BAU (Biological Allergen Units) is biological potency units as determined according to the requirements of the FDA for allergen product described in "Quantitative determination of relative potency of allergenic extracts" ("Methods of the allergen products testing Laboratory" "ELISA competition assay". Page 15, #49N-0012, FDA, October 1993). A dose of 100,000 SQ-Units containing grass extract equals a content of 2600-4700 BAU according to the method above. Likewise, other extracts can be assessed according to the method above.

Guidance to the normally applied, acceptable tests measuring bio-potency are found e.g. in Note for Guidance on Allergen Product; The European Agency for the Evaluation of Medicinal Product, CPMP_BWP_243_96, London, 1996.

An effective dose of an allergen for allergy vaccination or desensitization shall mean a dose which when taken once or repeatedly as incremental doses or as a repeated maintenance dose results in, for example, an adaptive immune response and thus serves as means to desensitize allergic patients. Preferably, the term shall mean the amount of allergen in each dosage form necessary to induce an adaptive immune response after repeated administration of said dosage forms in accordance with a treatment regimen.

The term "about" or "approximately" means within an acceptable range for the particular value as determined by one of ordinary skill in the art, which will depend in part on how the value is measured or determined, e.g., the limitations of the measurement system. For example, "about" can mean a range of up to 20%, preferably up to 10%, more preferably up to 5%, and more preferably still up to 1% of a given value.

The allergen used according to the invention may be derived from different sources.

Examples of naturally occurring allergens include pollen allergens (tree, herb, weed, and grass pollen allergens), insect allergens (inhalant, saliva and venom allergens, e.g. mite allergens, cockroach and midges allergens, hymenoptera venom allergens), animal hair and dander allergens (from e.g. dog, cat, horse, rat, mouse, etc.), and food allergens. Important pollen allergens from trees, grasses and herbs are such originating from the taxonomic orders of Fagales, Oleales, Pinales and Platanaceae including for example birch (*Betula*), alder (*Alnus*), hazel (*Corylus*), hornbeam (*Carpinus*) and olive (*Olea*), cedar (*Cryptomeria* and *Juniperus*), Plane tree (*Platanus*), the order of Poales including for example grasses of the genera *Lolium, Phleum, Poa, Cynodon, Dactylis, Holcus, Phalaris, Secale,* and *Sorghum,* the orders of Asterales and Urticales including for example herbs of the genera *Ambrosia, Artemisia,* and *Parietaria.* Other important inhalation allergens are those from house dust mites of the genus *Dermatophagoides* and *Euroglyphus,* storage mite e.g. *Lepidoglyphys, Glycyphagus* and *Tyrophagus,* those from cockroaches, midges and fleas e.g. *Blatella, Periplaneta, Chironomus* and *Ctenocepphalides,* and those from mammals such as cat (genus *Felis*), dog (genus *Canis*), cow (genus *Bos*) and horse (genus *Equus*), venom allergens including such originating from stinging or biting insects such as those from the taxonomic order of Hymenoptera including bees (superfamily Apidae), wasps (superfamily Vespidea), and ants (superfamily Formicoidae). Important inhalation allergens from fungi are, for example, those originating from the genera *Alternaria* and *Cladosporium.*

The pharmaceutical product of the invention may comprise at least two different allergens either originating from the same allergenic source or originating from different allergenic sources. For example the pharmaceutical product may comprise grass group 1, grass group 2/3, grass group 5 and grass group 6 allergens or mite group 1 and group 2 allergens from different grass and mite species respectively, weed antigens like short and giant ragweed allergens, different fungi allergens like *alternaria* and *cladosporium,* tree allergens like birch, hazel, hornbeam, oak and alder allergens, food allergens like peanut, soybean and milk allergens.

In a more specific embodiment of the invention the allergen may be selected from Bet v 1, Aln g 1, Cor a 1 and Car b 1, Que a 1, Cry j 1, Cry j 2, Cup a 1, Cup s 1, Jun a 1, Jun a 2, jun a 3, Ole e 1, Lig v 1, Pla l 1, Pla a 2, Amb a 1, Amb a 2, Amb t 5, Art v 1, Art v 2, Par j 1, Par j 2, Par j 3, Sal k 1, Ave e 1, Cyn d 1, Cyn d 7, Dac g 1, Fes p 1, Hol l 1, Lol p 1 and 5, Pha a 1, Pas n 1, Phl p 1, Phl p 5, Phl p 6, Poa p 1, Poa p 5, Sec c 1, Sec c 5, Sor h 1, Der f 1, Der f 2, Der p 1, Der p 2, Der p 7, Der m 1, Eur m 2, Gly d 1, Lep d 2, Blo t 1, Tyr p 2, Alt a 1, Bla g 1, Bla g 2, Per a 1, Fel d 1, Can f 1, Can f 2, Bos d 2, Equ c 1, Equ c 2, Equ c 3, Mus m 1, Rat n 1, Apis m 1, Api m 2, Ves v 1, Ves v 2, Ves v 5, Dol m 1, Dol m 2, Dol m 5, Pol a 1, Pol a 2, Pol a 5, Sol i 1, Sol i 2, Sol i 3 and Sol i 4, Alt a 1, Cla h 1, Asp f 1, Bos d 4, Mal d 1, Gly m 1, Gly m 2, Gly m 3, Ara h 1, Ara h 2, Ara h 3, Ara h 4, Ara h 5 or shufflant hybrids from Molecular Breeding (Maxygen, Inc.) of any of these.

In the most preferred embodiment of the invention the allergen is a grass pollen extract in the form of an extract of *Phleum pratense* pollen, or a mixture of pollen extracts from grass species such as *Dactylis glomerate, Festiuca, Lolium perenne, Phleum pratense* and *Festuca pratensis, Secale cereale,* or *Dactylis glomerate, Anthxanthum odoratum, Lolium perenne, Phleum pretense* and *Poa pratensis* or any other mixes of grass extract, a dust mite allergen in the form an extract of *Dermatophagoides farinae* or *Dermatophagoides pteronyssinus,* or a mixture of extracts of *Dermatophagoides farinae* and *Dermatophagoides pteronyssinus,* a tree pollen extract in the form of an extract of *Betula verrucosa,* or a mixture of pollen extracts from *Betula verrucosa, Alnus glutinosa* and *Corylus avellana* and/or *Carpinus betulus* and/or *Quercus alba,* an extract of ragweed pollen, such as extract of Ambrosia pollen, or cat allergen (e.g. extract of cat hair and/or dander or recombinant Fel d 1).

Allergy is also a known disease in animals especially domestic and companion ship animal. It is known in the art that they develop allergies toward numerous allergen sources including grass, house dust mites, and parasites. Hematophagous, i.e. bloodsucking insect infestation is known to lead to a hypersensitive response called flea allergic dermatitis (FAD). In a preferred embodiment of the current invention allergens for animal vaccines include allergens originating or transferred from parasites like ectoparasites (e.g. fleas, ticks, mosquitoes, flies), parasitic helminth venom (like heart worm e.g. *Dirofilaria* or onchocerciasis e.g. *Onchocerca*) and house dust mite. More preferred are saliva allergens from fleas like *Ctenocephalides* e.g. *C. canis* and *C. felis*, hard ticks likes *Ixodes, Amblyomma*, soft ticks like *Ornithodoros* and from midges like *Culicoides*.

The allergen incorporated into the pharmaceutical product of the invention may be in the form of an extract, a purified allergen, a modified allergen, a recombinant allergen or a mutant of a recombinant allergen. An allergenic extract may naturally contain one or more isoforms of the same allergen, whereas a recombinant allergen typically only represents one isoform of an allergen. In a preferred embodiment the allergen is in the form of an extract. In another preferred embodiment the allergen is a recombinant allergen or a mixture of recombinant allergens as separate proteins or as fusion proteins. In a further preferred embodiment the allergen is a naturally occurring low IgE-binding mutant or a recombinant low IgE-binding mutant.

In a further embodiment of the invention the low IgE binding allergen is an allergen according to WO 99/47680 or WO 02/40676 or PCT/DK03/00322 ("Allergen mutants").

Several laboratory tests are available for characterizing an allergen. The most widely used techniques are sodium dodecyl sulphate polyacrylamide gel electrophoresis (SDS-PAGE), isoelectric focusing (IEF), crossed immunoelectrophoresis (CIE) and Rocket Immuno Electrophoresis (RIE). The quantification of individual allergens may be performed by a variety of quantitative immunoelectrophoretic techniques (QIE), Radial Immune Diffusion (RIE) or by enzyme-linked immunosorbent assays (ELISA) and by MS quantification as described in PCT/DK2006/000480. The determination of total allergenic activity is most frequently performed by radio allergosorbent test (RAST), Magic Lite assay (LIA) or related techniques. ELISA-based techniques may also be used.

The classification of an allergen as a major allergen can be subject to several tests. An allergen is commonly classified as a major allergen if at least 25% of the patients shows strong IgE binding (score 3) and at least moderate binding (score 2) from 50% of the patients, the binding being determined by an CRIE (Crossed Radio Immune Electrophoresis) (CRIE Strong binding, i.e. visible IgE-binding on an X-ray film after one day; CRIE Moderate binding, i.e. binding after 3 days; CRIE Weak binding, i.e. binding after 10 days). Strong IgE binding from at least 10% of the patients classifies the allergen as an Intermediate allergen and clearly specific binding from less than 10% of the patients classifies it as a Minor allergen. Other methods may also be used in determining the IgE binding for instance IgE-blots.

In classical incremental dosage desensitization by the subcutaneous route using Alutard SQ, the dose of allergen is increased to a certain maximum typically 100.000 SQ-U/dose. According to the invention the dose of allergen is increased to a maximum dose which is between 5.000 and 50.000 SQ-U, more preferred between 5.000 and 30.000 SQ-U, preferred 5.000 to 10.000 SQ-U, or more preferred between 10.000 and 20.000 SQ-U, preferred between 12.000 and 17.000 SQ-U, or most preferred about 15.000 SQ-U.

According to the invention up-dosing is suitably carried out using 2-6 injections, more preferred 2 to 5 injections, more preferred 2 to 4 injections, more preferred 2 to 3 injections and most preferred 3 injections where increasing amount of allergen is administered until the maximum dose is reached. In one embodiment up-dosing is carried by 3 injections of compositions containing 300 SQ-U, 3000 SQ-U and 15.000 SQ-U.

The last injection in the up-dosing phase contains the maximum or maximal dose and the maintenance dose normally contain the same amount of allergen as the maximum, or maximal dose of the up-dosing phase.

Whatever the maximal/maximum dose of allergen in the up-dosing phase is and in which way it is quantified (amount of extract, amount of major allergen, amount of clinically important allergen, SQ-U, BAU, IR etc) the up-dosing may suitably be carried out using 3 injections, the first injection containing an amount of allergen which is $1/10$ of the amount of allergen in injection number 2 and injection number 2 containing an amount of allergen which is $1/5$ of the amount of allergen in the third injection of the up-dosing phase.

Whatever the maximal/maximum dose of allergen in the up-dosing phase is and in which way it is quantified (amount of extract, amount of major allergen, amount of clinically important allergen, SQ-U, BAU, IR etc) the up-dosing may suitably be carried out using 5 injections, the first injection containing an amount of allergen which is $1/50$ of the amount of allergen in the maintenance dose, injection number 2 containing an amount of allergen which is $1/25$ of the amount of allergen in the maintenace dose, injection number 3 containing an amount of allergen which is $1/5$ of the amount of allergen in the maintenace dose, injection number 4 containing an amount of allergen which is $2/5$ of the amount of allergen in the maintenace dose, and injection number 5 the maintenance dose.

In the maintenance phase the maximal dose is repeated and is e.g a dose between 5.000 and 50.000 SQ-U, more preferred between 5000 and 30.000 SQ-U, more preferred between 10.000 and 20.000 SQ-U, preferred between 12.000 and 17.000 SQ-U or most preferred about 15.000 SQ-U is administered every 4-8 weeks, suitably every 6 weeks.

When expressed in BAU, the dose of allergen according to the invention is increased to a certain maximum dose which is between 130 and 2350 BAU, more preferred between 130 and 1410 BAU, more preferred between 260 and 940 BAU, preferred between 312 and 799 BAU or most preferred between 390 and 705 BAU.

The up-dosing may be carried out with 2-6 subcutaneous injections, more preferred 2 to 5 subcutaneous injections, more preferred 2 to 4 subcutaneous injections, more preferred 2 to 3 subcutaneous injections and most preferred 3 subcutaneous injections gradually increasing the amount of allergen until the maximal dose is reached.

In one embodiment up-dosing is carried using 3 subcutaneous injections with increasing doses of allergen where the first subcutaneous injection comprising 7.8 to 14.1 BAU, the second subcutaneous injection comprising 78 to 141 BAU and the third subcutaneous injection comprising 390-705 BAU.

In the maintenance phase the maximal dose is repeated, e.g between 130 and 2350 BAU, more preferred between 130 and 1410 BAU, more preferred between 260 and 940 BAU, more preferred between 312 and 799 BAU or most preferred between 390 and 705 BAU is administered every 4 to 8 weeks, suitably 6 weeks.

1 mg allergen extract normally contains between 100,000 and 1,000,000 SQ-unit. This means that 100,000 SQ are contained in from 0.1 mg extract to 1 mg allergen extract. In a similar manner, any SQ dose may be transformed into an allergen extract dose range. On this basis, the above dose ranges given in SQ may be recalculated into dose ranges in mg or μg allergen extract, wherein for the lower SQ limit of a range, the lower limit of the corresponding allergen extract range is used, and wherein for the upper SQ limit of a range, the upper limit of the corresponding allergen extract range is used.

Thus, in a further embodiment according to the invention the allergen is an allergen extract and the dose of extract is increased to a certain maximum dose which is between 0.005 and 0.5 mg, more preferred between 0.005 and 0.3 mg extract, more preferred between 0.01 and 0.2 mg extract, preferred between 0.012 and 0.17 mg extract or most preferred between 0.015 and 0.15 mg extract.

The up-dosing is carried out with 2-6 subcutaneous injections more preferred 2 to 5 subcutaneous injections, more preferred 2 to 4 subcutaneous injections, more preferred 2 to 3 injections and most preferred 3 subcutaneous injections gradually increasing the dose of extract until the maximum dose is reached. In one embodiment up-dosing is carried using 3 subcutaneous injections of increasing doses of allergen, the first injection comprising 0.3 μg to 3 μg extract, the second injection comprising 3 μg to 0.03 mg extract and the third injection comprising 15 μg to 0.15 mg extract.

In the maintenance phase the maximum dose is repeated, i.e. a dose between 0.005 and 0.5 mg extract, more preferred between 0.005 and 0.3 mg extract, more preferred between 0.01 and 0.2 mg extract, more preferred between 0.012 and 0.17 mg extract or most preferred a dose between 0.015 and 0.15 mg extract is administered every 4-8 weeks, suitably every 6 weeks.

As mentioned above the content of major allergens in an extract is one of the most important factors contributing to the bio-potency of the composition. The amount of major allergen in a composition may therefore be used as a measure of the strength of the composition.

Thus, in a further embodiment according to the invention the maximum dose of allergen is a dose comprising 0.25 μg to 100 μg, more preferred 0.25 to 75 μg, more preferred 0.25 to 45 μg, more preferred 0.4 μg to 30 μg, more preferred of 0.5 μg to 25 μg, even more preferred 0.6 to 22.5 μg of major allergen(s).

The up-dosing is suitable carried out using 2-6 subcutaneous injections, more preferred 2 to 5 subcutaneous injections, more preferred 2 to 4 subcutaneous injections, more preferred 2 to 3 subcutaneous injections and most preferred 2 injections or 3 injections gradually increasing the amount of allergen until the maximum dose is reached.

Alternatively, the up-dosing is carried out using 3 to 8 subcutaneous injections, more preferred 4 to 7 injections, more preferred 5 to 6 subcutaneous injections and most preferred 5 subcutaneous injections with increasing amount of allergen. Preferred the 5 injections is given with 7 days or 1 week between the injections.

In another alternative, the up-dosing is carried out using 6 to 9 subcutaneous injections, more preferred 7 to 8 subcutaneous injections and most preferred 8 subcutaneous injections with increasing amount of allergen.

In another alternative the updosing is carried out using 4, 6 or 7 injections.

In one embodiment up-dosing is carried using 3 subcutaneous injections with increasing doses of allergen, the first injection comprising 0.012 μg to 0.45 μg major allergen(s), the second injection comprising 0.12 μg to 4.5 μg major allergen(s) and the third injection comprising 0.6 μg to 22.5 μg major allergen(s).

In another embodiment the up-dosing phase comprises 5 subcutaneous injections with an increasing dose of allergen, the first injection comprising 0.012 μg to 0.45 μg major allergen(s), the second injection comprising 0.024 μg to 0.9 μg major allergen(s), the third injection comprising 0.12 μg to 4.5 μg major allergen(s), the fourth injection comprising 0.24 μg to 9 μg major allergen(s) and the fifth injection comprising 0.6 μg to 22.5 μg major allergen(s). Preferred the 5 injections is given with 7 days or 1 week between the injections.

In yet another embodiment the up-dosing phase comprises 8 subcutaneous injections with an increasing dose of allergen, the first injection comprises 3.6 ng to 0.135 μg major allergen(s), the second injection comprising 0.012 μg to 0.45 μg major allergen(s), the third injection comprising 0.024 to 0.9 μg major allergen(s), the fourth injection comprising 0.06 to 2.25 μg major allergen(s), the fifth injection comprising 0.12 μg to 4.5 μg major allergen(s), the sixth injection injection comprising 0.24 μg to 9 μg major allergen(s), the seventh injection comprises 0.36 to 13.5 μg major allergen(s), and the eight injection comprising 0.6 μg to 22.5 μg major allergen(s).

In another embodiment the updosing phase comprises 4, 6, or 7 subcutaneous injections, where the highest dose is 0.6 μg to 22.5 μg major allergen(s).

The content of major allergen(s) may be accounted for by several major allergens depending on the allergen source in question. Normally the number of major allergens is in the range of 1-10, mostly 1-5.

Major allergens are grass group 1 allergen e.g. phl p 1, loI p 1, sor h 1, dac g 1, cyn d 1, hol l 1, pha a 1, grass group 2/3 allergen e.g. phl p 2/3, loI p 2/3, grass group 5 allergen e.g. phl p 5, loI p 5, dac g 5, poa p 5, grass group 6 allergen e.g. phl p 6, poa p 6, tree pollen group 1 allergen e.g. bet v1, aln g 1, coral, car b 1, mite group 1 allergen e.g. der p 1, der f 1, eur m 1, mite group 2 allergen e.g. der p 2, der f 2, eur m2, cat allergen e.g. fel d 1, alternaria group 1 allergen, e.g. Alt a 1, olive pollen group 1 allergen, e.g. Ole e 1, parietaria group 1 allergen, e.g. Par j 1, cedar group 1 and group 2 allergen e.g. cry j 1, cry j 2, Artemisia group 1 allergen e.g. Art v 1 and short or giant ragweed pollen allergen e.g. amb a 1, amb a 2, amb 1, amb t 2, ect.

Classification of an allergen in according to its relevance in allergy vaccination may suitable be based on an assessment of the clinical importance of the particular allergen. The single clinically most important major allergen is the allergen from a particular allergen source (e.g. pollen) that is responsible for a majority of the adaptive immune responses following the desensitization process. Examples of clinically important major allergens include group 5 allergens from grasses (e.g. Phl p 5), group 1 allergens from trees (e.g. Bet v 1), group 1 allergen from dust mites (e.g. Der p 1 or Der f 1) and/or group 2 allergen (Der f 2 and Der p 2), cedar pollen allergen 1 and 2 (e.g. Cry j 1, Cry j 2), ragweed pollen 1 and 2 (Amb a 1, Amb a 2), cat allergen 1 (i.e. Fel d 1).

Thus, according to a further embodiment of the invention the maximum or maintenance dose of clinically important major allergen is 0.025 to 10.5 μg, more preferred 0.025 to 6.3 μg, more preferred 0.05 μg to 4.2 μg, more preferred 0.06 μg to 3.6 μg, even more preferred 0.075 μg to 3.15 μg of clinically important major allergen.

The up-dosing is carried out with 2-6 subcutaneous injections, more preferred 2 to 5 subcutaneous injections, more preferred 2 to 4 subcutaneous injections, more preferred 2 to 3 subcutaneous injections and most preferred 2 subcutaneous injections or 3 subcutaneous injections gradually increasing the amount of allergen until the maximal dose or maintenance of clinically important major allergen(s) is reached.

Alternatively, the up-dosing is carried out using 3 to 8 subcutaneous injections, more preferred 4 to 7 injections, more preferred 5 to 6 subcutaneous injections and most preferred 5 subcutaneous injections with increasing amount of allergen until the maximal dose or maintenance dose of clinically important major allergen(s) is reached.

In another alternative, the up-dosing is carried out using 6 to 9 subcutaneous injections, more preferred 7 to 8 subcutaneous injections and most preferred 8 subcutaneous injections with increasing amount of allergen until the maximal dose or maintenance dose of clinically important major allergen(s) is reached.

In another embodiment the updosing phase comprises 4, 6, or 7 subcutaneous injections, until the maximal dose of clinically important major allergen(s) is reached.

The maintenance dose is suitably about 0.05 µg to 4.2 µg, more preferred 0.06 µg to 3.6 µg, even more preferred 0.075 µg to 3.15 µg clinically important major allergen.

In one embodiment up-dosing is carried using 3 subcutaneous injections with increasing doses of allergen, the first injection comprising 0.001 µg to 0.084 µg clinically important major allergen, the second injection comprises 0.01 µg to 0.84 µg clinically important major allergen and the third injection comprises 0.05 µg to 4.2 µg clinically important major allergen.

In another embodiment up-dosing is carried using 3 subcutaneous injections with increasing doses of allergen, the first injection comprising 0.0015 µg to 0.063 µg clinically important major allergen, the second injection comprises 0.015 µg to 0.63 µg clinically important major allergen and the third injection comprises 0.075 µg to 3.15 µg clinically important major allergen.

In another embodiment the up-dosing phase comprises 5 subcutaneous injections with an increasing dose of allergen, the first injection comprising 0.0015 µg to 0.063 µg of clinically important major allergen, the second injection comprising 0.003 µg to 0.126 µg of clinically important major allergen, the third injection comprising 0.015 µg to 0.63 µg of clinically important major allergen, the fourth injection comprising 0.03 µg to 1.26 µg of clinically important major allergen, and the fifth injection comprises comprising 0.075 µg to 3.15 µg of clinically important major allergen, In still another embodiment the up-dosing phase comprises 8 subcutaneous injections with an increasing dose of allergen, the first injection comprising 0.45 ng to 0.189 µg of clinically important major allergen, the second injection comprising 0.0015 µg to 0.063 µg of clinically important major allergen, the third injection comprising 0.003 µg to 0.126 µg of clinically important major allergen, fourth injection comprising 0.075 µg to 0.315 µg of clinically important major allergen, the fifth injection comprising 0.015 µg to 0.63 µg of clinically important major allergen, the sixth injection comprising 0.03 µg to 1.26 µg of clinically important major allergen, the seventh injection comprising 0.045 µg to 1.89 µg of clinically important major allergen and the eight injection comprises comprising 0.075 µg to 3.15 µg of clinically important major allergen.

Clinically important major allergens are as indicated above Dac g 5, Fes p 5, Lol p 5, Phl p 5, Poa p 5, Sec c 5, Bet v 1, Aln g 1, Cor a 1, Car b 1, Que a 1, Ole e 1, Par j 1, Der p 1, Der f 2, Der f 1, Der f 2, Amp a 1 and or Amb a 2 and Fel d 1. More clinically important (major) allergens are known to the skilled person.

In one specific embodiment of the invention the allergen is a grass pollen allergen, a mixture of grass pollen allergens, a grass pollen extract or a mixture of grass pollen extracts. For grasses the clinically most important allergen is the group 5 allergens. The maintenance dose or maximal dose in the up-dosing phase is typically 0.1 to 10 µg, more preferred 0.5 to 6 µg, more preferred 1 to 4 µg, more preferred 1.2 to 3.4 µg, or even more preferred about 1.5 µg to about 3 µg group 5 allergen for a single species (e.g. *Phleum pratense*) and for mixtures of grass pollen extracts, the total amount of group 5 allergens from the different grass species (e.g. Dac g 5, Fes p 5, Lol p 5, Phl p 5, Poa p 5 and Sec c 5) is also, typically 0.1 to 10 µg, more preferred 0.5 to 6 µg, more preferred 1 to 4 µg, more preferred 1.2 to 3.4 µg, even more more preferred about 1.5 µg to about 3 µg.

In one specific embodiment of the invention the allergen is a tree pollen allergen, a mixture of tree pollen allergens, a tree pollen extracts or a mixture of tree pollen extracts. For tree pollens the clinically most important allergen is the group 1 allergens. The maintenance dose or the maximal dose in the up-dosing phase is typically 0.1 to 10 µg, more preferred 0.5 to 6 µg, more preferred 1 to 4 µg, more preferred 1.2 to 3.4 µg, or even more preferred about 1.5 µg to about 3 µg group 1 allergen for a single species (e.g. *Betula verrucosa*), and for mixtures of tree pollen extracts the total amount of group 1 allergens from the different species (e.g. Bet v 1, Aln g 1, Cor a 1, or Car b 1, Que a 1) is also typically 0.1 to 10 µg, more preferred 0.5 to 6 µg, more preferred 1 to 4 µg, more preferred 1.2 to 3.4 µg, or even more preferred about 1.5 µg to about 3 µg.

The up-dosing is suitably carried out with 2-6 subcutaneous injections, more preferred 2 to 5 subcutaneous injections, more preferred 2 to 4 subcutaneous injections, more preferred 2 to 3 subcutaneous injections and most preferred 2 subcutaneous injections or 3 subcutaneous injections gradually increasing the amount of allergen until the maximal dose is reached.

Alternatively, the up-dosing is carried out using 3 to 8 subcutaneous injections, more preferred 4 to 7 injections, more preferred 5 to 6 subcutaneous injections and most preferred 5 subcutaneous injections with increasing amount of allergen.

In another alternative, the up-dosing is carried out using 6 to 9 subcutaneous injections, more preferred 7 to 8 subcutaneous injections and most preferred 8 subcutaneous injections with increasing amount of allergen.

In another alternative, the up-dosing is carried out using 4, 6, or 7 subcutaneous injections.

According to a preferred embodiment the up-dosing phase comprises 3 subcutaneous injections with increasing doses of allergen, the first injection comprising about 0.03 µg to about 0.06 µg of grass group 5 or tree group 1 allergen, the second injection comprising about 0.3 µg to about 0.6 µg grass group 5 or tree group 1 allergen and the third injection comprising about 1.5 µg to about 3 µg of grass group 5 or tree group 1 allergen, provided that all 3 injections contain either tree or grass allergen.

According to another preferred embodiment the up-dosing phase comprises 3 subcutaneous injections with increasing doses of allergen, the first injection comprising about 0.01 µg to about 0.12 µg of grass group 5 or tree group 1 allergen, the second injection comprising about 0.1 µg to about 1.2 µg grass group 5 or tree group 1 allergen and the third injection comprising about 0.5 µg to about 6 µg of grass group 5 or tree group 1 allergen, provided that all 3 injections contain either tree or grass allergen.

In another embodiment the up-dosing phase comprises 5 subcutaneous injections with an increasing dose of allergen, the first injection comprising about 0.03 µg to about 0.06 µg of grass group 5 allergen or tree group 1 allergen, the second injection comprising about 0.06 µg to about 0.12 µg of grass group 5 allergen or tree group 1 allergen, the third injection comprising about 0.3 µg to about 0.6 µg of grass group 5 allergen or three group 1 allergen, the fourth injection comprising about 0.6 µg to about 1.2 µg of grass group 5 allergen or three group 1 allergen and the fifth injection comprising about 1.5 µg to about 3 µg of grass group 5 allergen or three group 1 allergen, provided that all 5 injections contain either tree or grass allergen.

According to another preferred embodiment the up-dosing phase comprises 5 injections with increasing doses of allergen, the first injection comprising about 0.01 µg to about 0.06 µg of grass group 5 or tree group 1 allergen, the second injection comprising about 0.02 µg to about 0.12 µg grass group 5 or tree group 1 allergen, the third injection comprising about 0.1 µg to about 1.2 µg of grass group 5 or tree group 1 allergen, the fourth injection comprising about 0.2 µg to about 1.2 µg of grass group 5 or tree group 1 allergen, and the fifth injection comprises about 0.5 µg to about 6 µg of grass group 5 or tree group 1 allergen where all 3 injections contain either tree or grass allergen.

In still another embodiment the up-dosing phase comprises 8 subcutaneous injections with an increasing dose of allergen, the first injection comprising about 0.009 µg to about 0.018 µg of grass group 5 allergen or tree group 1 allergen, the second injection comprising about 0.03 µg about 0.06 µg of grass group 5 allergen or tree group 1 allergen, the third injection comprising about 0.06 µg to about 0.12 µg of grass group 5 allergen or tree group 1 allergen, the fourth injection comprising about 0.15 µg to about 0.3 µg of grass group 5 allergen or tree group 1 allergen, the fifth injection comprising about 0.3 µg to about 0.6 µg of grass group 5 allergen or three group 1 allergen, the sixth injection comprising about 0.6 µg to about 1.2 µg of grass group 5 allergen or three group 1 allergen, the seventh injection comprising about 0.9 µg to about 1.8 µg of grass group 5 allergen or three group 1 allergen and the eight injection comprising about 1.5 µg to about 3 µg of grass group 5 allergen or three group 1 allergen, provided that all 8 injections contain either tree or grass allergen.

In another alternative, the up-dosing is carried out using 4, 6, or 7 injections of grass group 5 allergen or tree group 1 allergen.

In one specific embodiment of the invention the allergen is a mite allergen, a mixture of mite allergens, an extract of one mite species or a mixture of extracts from different mite species. For mites the clinically most important allergen is the group 1 allergens although the group 2 allergens are also important. The maximal dose in the up-dosing phase is suitably about 0.1 to about 7.5, more preferred about 0.25 to about 4.5, more preferred about 0.5 to about 3, more preferred about 0.6 to about 2.5, or more preferred about 0.75 µg to about 2.25 µg of group 1 allergen from a single mite species (for example 0.75 µg to 2.25 µg of Der p 1 or Der f 1 allergen) and for mixtures of extracts of mites such as *Dermatophagoides farinae* and *Dermatophagoides ptheronyssinus*, the total amount of group 1 allergens from the different species (e.g. Der p 1 and Der f 1) is also about 0.1 to about 7.5, more preferred about 0.25 to about 4.5, more preferred about 0.5 to about 3, or more preferred about 0.6 to about 2.5, more preferred about 0.75 µg to about 2.25 µg. The amount of group 2 allergen in mite extracts is typically ⅟₁₅ to ½ of the amount of group 1 allergen.

The up-dosing is suitably carried out with 2-6 subcutaneous injections, more preferred 2 to 5 subcutaneous injections, more preferred 2 to 4 subcutaneous injections, more preferred 2 to 3 subcutaneous injections and most preferred 2 subcutaneous injections or 3 subcutaneous injections gradually increasing the amount of mite group 1 allergen until the maximal dose is reached.

Alternatively, the up-dosing is carried out using 3 to 8 subcutaneous injections, more preferred 4 to 7 injections, more preferred 5 to 6 subcutaneous injections and most preferred 5 subcutaneous injections with increasing amount of mite group 1 allergen.

In another alternative, the up-dosing is carried out using 6 to 9 subcutaneous injections, more preferred 7 to 8 subcutaneous injections and most preferred 8 subcutaneous injections with increasing amount of mite group 1 allergen.

In another alternative, the up-dosing is carried out using 4, 6, or 7 injections of or mite group 1 allergen.

According to one preferred embodiment the up-dosing phase comprises 3 subcutaneous injections with an increasing dose of allergen, the first injection comprising about 0.005 µg to about 0.09 µg mite group 1 allergen, the second injection comprising about 0.05 µg to about 0.9 µg of mite group 1 allergen and the third injection comprising about 0.25 µg to about 4.5 µg to of mite group 1 allergen.

According to another preferred embodiment the up-dosing phase comprises 3 subcutaneous injections with an increasing dose of allergen, the first injection comprising about 0.015 µg to about 0.045 µg mite group 1 allergen, the second injection comprising about 0.15 µg to about 0.45 µg of mite group 1 allergen and the third injection comprising about 0.75 µg to about 2.25 µg to of mite group 1 allergen.

According to another embodiment the up-dosing phase comprises 5 subcutaneous injections with an increasing dose of allergen, the first injection comprising about 0.015 µg to about 0.045 µg of mite group 1 allergen, the second injection comprising about 0.03 µg to about 0.09 µg of mite group 1 allergen, the third injection comprising about 0.15 µg to about 0.45 µg of mite group 1 allergen, the fourth injection comprising about 0.3 µg to about 0.9 µg of mite group 1 allergen and the fifth injection comprising about 0.75 µg to about 2.25 µg of mite group 1 allergen.

According to another embodiment the up-dosing phase comprises 5 injections with an increasing dose of allergen, the first injection comprising about 0.005 µg to about 0.09 µg of mite group 1 allergen, the second injection comprising about 0.01 µg to about 0.18 µg of mite group 1 allergen, the third injection comprising about 0.05 µg to about 0.9 µg of mite group 1 allergen, the fourth injection comprising about 0.1 µg to about 1.8 µg of mite group 1 allergen and the fifth injection comprising about 0.25 µg to about 4.5 µg of mite group 1 allergen.

According to another embodiment the updosing phase 4, 6, or 7 injections with an increasing dose of allergen to reach a maximal dose or maintenance dose.

According to another embodiment the up-dosing phase comprises 8 subcutaneous injections with an increasing dose of allergen, the first injection comprising about 0.0045 µg to about 0.0135 µg of mite group 1 allergen, the second injection comprising about 0.015 µg to about 0.045 µg of mite group 1 allergen, the third injection comprising about 0.03 µg to about 0.09 µg of mite group 1 allergen, the fourth injection comprising about 0.075 µg to about 0.225 µg of mite group 1 allergen, the fifth injection comprising about 0.15 µg to about 0.45 µg of mite group 1 allergen, the sixth injection comprising about 0.3 µg to about 0.9 µg of mite group 1 allergen, the seventh injection comprising about 0.45 µg to about 1.35 µg of mite group 1 allergen, and the eight injection about 0.75 µg to about 2.25 µg of mite group 1 allergen.

According to a further embodiment of the invention the allergen is an olive pollen allergen, a mixture of olive pollen allergens, an olive pollen extract or mixture of olive pollen extracts and the amount of olive group 1 allergen in the last injection of the up-dosing phase is 0.2 µg to 1.8 µg, more preferred 0.2 µg to 1 µg, or 0.2 µg to 0.4 µg, more preferred 0.4 µg to 0.7 µg, more preferred 0.4 µg to 0.6 µg more preferred about 0.55 µg of olive pollen group 1 allergen.

According to still another embodiment of the invention the allergen is a parietaria pollen allergen, a mixture of parietaria pollen allergens, an parietaria pollen extract or mixture of parietaria pollen extracts and the amount of parietaria pollen group 1 allergen in the last injection of the up-dosing phase is 0.3 µg to 3 µg, more preferred 0.3 µg to 1.7 µg, more preferred 0.6 µg to 1.2 µg, or 0.3 µg to 0.6 µg, more preferred 0.7 µg to 1 µg and more preferred about 0.9 µg of parietaria pollen group 1 allergen.

According to another embodiment the allergen is a alternaria allergen, a mixture of alternaria allergens, an altarnaria extract or mixture of alternaria extracts and the amount of alternaria group 1 allergen in the last injection of the up-dosing phase is 0.025 to 0.25 µg, more preferred 0.025 to 0.15 µg, more preferred 0.025 to 0.05 µg, or more preferred 0.05 to 0.1 µg, more preferred 0.06 to 0.085 µg and most preferred about 0.075 µg *Alternaria* group 1 allergen, such as Alt a 1.

According to another embodiment of the invention the allergen is a Artemisia pollen allergen, a mixture of Artemisia pollen allergens, an Artemisia pollen extract or mixture of Artemisia pollen pollen extracts and the amount of Artemisia group 1 allergen in the last injection of the up-dosing phase is 0.45 to 4.5 µg, more preferred 0.45 to 2.7 µg, more preferred 0.45 to 0.9 µg, or more preferred 0.9 to 1.8 µg, more preferred 1 to 1.5 µg and most preferred about 1.4 µg Artemisia group 1 allergen, such as Art v 1.

The pharmaceutical product may also contain one or more units comprising the composition used for the maintenance phase. Suitably, the maintenance dose is the same as the dose in the last injection in the up-dosing phase.

According to this embodiment of the invention the pharmaceutical product comprises one or more units comprising said composition and wherein the pharmaceutical product is provided in a form for administration by subcutaneous injections characterized in that one dose contain:

a) 0.25 µg to 100 µg, more preferred 0.25 µg to 75 µg, more preferred 0.25 µg to 45 µg, more preferred 0.4 µg to 30 µg, more preferred of 0.5 µg to 25 µg, even more preferred 0.6 to 22.5 µg of major allergen(s); or b) about 0.025 to about 10 µg, more preferred about 0.025 to about 6.3 µg, more preferred about 0.05 µg to about 4.2 µg, more preferred about 0.05 µg to about 3.6 µg, even more preferred about 0.075 µg to about 3.15 µg of clinically important major allergen; or c) about 0.1 µg to about 10.5 µg, more preferred about 0.5 µg to about 6 µg, more preferred about 1 µg to about 4 µg, more preferred about 1.2 µg to about 3.4 µg, more preferred about 1.5 µg to about 3 µg group 5 allergen from grass or group 1 allergen from threes; or d) about 0.1 µg to about 7.5 µg, more preferred about 0.25 µg to about 4.5 rig, more preferred about 0.5 µg to about 3 µg, more preferred about 0.6 µg to about 2.5 µg, more preferred about 0.75 µg to about 2.25 µg mite group 1 allergen, and in that the amount; or e) 0.2 µg to 1.8 µg, more preferred 0.2 µg to 1 µg, more preferred 0.4 µg to 0.7 µg or 0.2 to 0.4 µg, more preferred 0.4 µg to 0.6 µg more preferred about 0.5 µg of olive pollen group 1 allergen; or f) 0.3 µg to 3 µg, more preferred 0.3 µg to 1.7 µg, more preferred 0.6 µg to 1.2 µg or 0.3 to 0.6 µg, more preferred 0.7 µg to 1 µg and more preferred about 0.59 µg of parietaria pollen group 1 allergen; or g) 0.45 to 4.5 µg, more preferred 0.45 to 2.7 µg, more preferred 0.45 to 0.9 µg, or more preferred 0.9 to 1.8 µg, more preferred 1 to 1.5 µg and most preferred about 1.4 µg Artemisia group 1 allergen, such as Art v 1; or h) 0.025 to 0.25 µg, more preferred 0.025 to 0.15 µg, more preferred 0.025 to 0.05 µg, or more preferred 0.05 to 0.1 µg, more preferred 0.06 to 0.085 µg and most preferred about 0.075 µg *Alternaria* group 1 allergen, such as Alt a 1.

Maintenance dose is given every 4-8 weeks suitable every 6 weeks.

The clinically important major allergen(s) may be comprised in an allergen extract or be recombinantly produced. Recombinant major allergens may be used in the same amount as in allergen extracts comprising such major allergen or in higher doses. Higher doses are believed to be more effective, but are also believed to be associated with a risk of potentially more frequent or more severe side effects.

For hypoallergenic variants of major allergens, i.e. allergens with a decreased ability to caused immediate or late phase allergic reactions, a dosage form according to the invention preferably contains 10-100 times more major allergen per dosage form. Such hypoallergenic variants may be of recombinant or natural origin.

The allergen content of a dosage form according to the invention can be determined by routine immune assays such as CIE (Cross Immune Electrophoresis), RIE (Radio Immune Electrophoresis) and SDS-PAGE (Sodium Dodecyl Sulphate Poly Acrylamide Gel Electrophoresis), MS quantification as described in PCT/DK2006/000480 and immune assays such as ELISA and Magic Like Specific IgE assay (LIA).

Treatment of in particular seasonal allergies such as hay fever is normally associated with a particular time of year were exposure to the offending allergen is present or elevated. The allergen season will vary with the allergen source e.g. the pollen and the climatic conditions for the allergen source in the particular territory. Thus, the season for an allergen will differ in one part of the world from another part of the world depending on the climate, but will normally fall within the same period of the year for the same territory varying with the actual conditions of that year (see for instance "Aerobiology and inhalant allergies", Chapter 19, T.A.E. Platts-Mills & W. R. Solomon (Ed. S. Manning) 1993, Mosby-Year Book, St. Louis). It is well known to a skilled person when a season is normally expected to start for a particular allergen in a particular region.

In one embodiment of the invention methods of treatment is provided including a pre-seasonal treatment i.e. an administration of pharmaceutical product according to the invention before the allergen season. In a particularly preferred embodiment the pre-seasonal treatment period comprises administration of pharmaceutical product according to the invention for a period of more than 2 weeks prior to the allergen season, more preferably between 4-20 weeks, most preferably between 8-12 weeks.

The pharmaceutical composition of the invention may also be used without pre-seasonal treatment and may be starte in the season according to WO 08 116936, The pharmaceutical compositions according to the invention may or may not contain an adjuvant. The adjuvant may suitably be selected from well known adjuvants such as oxygen containing metal salts (aluminium hydroxide and calcium phospahate), heat-labile enterotoxin (LT), cholera toxin (CT), cholera toxin B subunit (CTB), polymerised liposomes, mutant toxins, e.g. LTK63 and LTR72, microcapsules, interleukins (e.g. IL-1β, IL-2, IL-7, IL-12, INFγ), GM-CSF, MDF derivatives, CpG oligonucleotides, LPS, MPL, phosphophazenes, Adju-Phos®, glucan, antigen formulation, liposomes, DDE, DHEA, DMPC, DMPG, DOC/Alum Complex, Freund's incomplete adjuvant, ISCOMs®, LT Oral Adjuvant, muramyl dipeptide, monophosphoryl lipid A (MPL), muramyl tripeptide, or phospatidylethanolamine.

In one embodiment the pharmaceutical composition of the inventinon does not contain an adjuvant.

However, the pharmaceutical compositions according to the invention preferably contain allergen adsorbed to aluminium hydroxide which is a well known adjuvant.

The aluminium hydroxide has a depot effect which means that the active substance will be released gradually from the vaccine. This is believed to have a number of beneficial effects, e.g. prolonged stimulation, beneficial drug release, and protection of the biological interactive substances against environmental conditions.

It is further believed that the aluminium hydroxide may possess certain entrapment properties, thus retaining the active substance to be delivered.

Another feature of aluminium hydroxide is the protection of the active substance either by maintaining the ideal pH for the active substance in the microenvironment, thus preventing acid degradation, or by protecting the active substance against enzymatic degradation thereby allowing the substance to be delivered.

Furthermore, aluminium hydroxide may have a buffer capacity. This may result in an in vivo microenvironment within the vaccine formulation, which protects the active substance from the degradable environment.

According to the invention the ratio of number of SQ-U units to amount of Al (ion) is typically 15.000 SQ-U to 0.3 to 0.8, more preferred 0.5 to 0.6 mg Al (ion) or most preferred 15.000 SQ-U to 0.565 mg Al (ion).

Suitably the ratio of allergen to Al (aluminum ion) is the same throughout the up-dosing phase and the maintenance phase where aluminum hydroxide is present in the compositions in an amount corresponding to 0.3 to 0.8 mg Al, more preferred 0.5 to 0.6 mg Al, or most preferred about 0.565 mg Al per maintenance dose of allergen (or maximal dose) as described above.

Expressed as a ratio of the amount in μg of major allergen(s) to amount of Al in mg the compositions of the invention, the ratio is 1 to 45, preferably 1 to 40.

Expressed as a ratio of the amount of the clinically important allergen in μg to amount of Al in mg in the compositions of the invention the ratio is 0.04 to 11, more preferred 0.1 to 6. This ratio is normally the same for the doses in the up-dosing phase and the maintenance phase.

Expressed as the ratio of grass group 5 allergen, tree group 1 allergen, mite group 1 allergen, olive group 1 allergen, parietaria group 1 allergen, Artemisia group 1 allergen, *Alternaria* group 1 allergen to Al (aluminium ion) in the compositions of the invention the ratio is the maintenance as described above divided by 0.565.

The compositions of the present invention may be prepared by adding the aluminium hydroxide (e.g. Alhydrogel) to a solution containing allergen and allowing the allergen and aluminium hydroxide to react for a period of time. The reaction period may be from 0.1 to 48 hours, preferably from 12 to 24 hours. The reaction is preferably carried out at a temperature of from 4 to 45° C., more preferably from 4 to 20° C.

A composition containing 30.000 SQ-U may be prepared by diluting Alutard SQ containing 100.000 SQ-U/ml and 1.13 mg Al/ml to 30.000 SQ-U/ml and adding aluminium hydroxide to reach an Al concentration of 1.13 mg Al/ml. One particular way of obtaining an allergen composition comprising 30.000 SQ-U/ml and 0.565 mg Al would therefore be to add 2⅓ ml of an aqueous suspension containing 1.13 mg Al/ml to each 1 ml of Alutard SQ containing 100.000 SQ-U/ml. Other formulations of the invention may be prepared in a similar manner. Alutard SQ containing 100.000 SQ-U/ml and 1.13 mg Al (aluminium ion)/ml are commercially available.

It is to be understood that the formulation of the invention may further comprise additional adjuvants and other excipients suitable for such type of formulation. Such additional adjuvants and excipients are well-known to the person skilled in the art and include i.a. solvents, emulsifiers, wetting agents, plasticizers, colouring substances, fillers, preservatives, viscosity adjusting agents, buffering agents, mucoadhesive substances, and the like. Examples of formulation strategies are well-known to the person skilled in the art.

As used herein allergy vaccination or desensitization includes both treatment and prevention of allergy. By the term "treatment" is meant partly of wholly curing, alleviating symptoms or inhibiting causes of symptoms. The term "prevention" means prophylactic treatment.

Example 1

According to the invention up-dosing may be carried out in a flexible and fast way using the schedule described below:

Only 2 concentrations of the formulation is required and the maintenance dose can be reached with 3 injections in 3 days and up to 4 weeks.

Up-dosing schedule:

TABLE 2

| Injection number | Vial | Injection volume in ml* | administered dose |
|---|---|---|---|
| 1 | Vial A 600 SQ-E/ml | 0.5 | 300 SQ-E |
| 2 | Vial B | 0.1 | 3000 SQ-E |
| 3 | 30.000 SQ-E/ml | 0.5 | 15.000 SQ-E |

Injection intervals: injection intervals: 1-14 days

If interval exceeds 2-3 weeks: Repeat last dose (300 or 3.000 SQ-E)

If interval→3 weeks: Restart with vial A 15.000 SQ-E corresponds to 0.6 to 22.5 μg of major allergen(s), 0.075 μg to 3.15 μg of clinically important major allergen, 1.5 μg to 3 μg group 5 allergen from grass or group 1 allergen from trees; or 0.75 μg to 2.25 μg mite group 1 allergen, about 0.55 μg olive group 1 allergen, about 0.9 μg *Parietaria* group 1 allergen, about 1.4 μg Artemisia group 1 allergen and about 0.075 μg *Alternaria* group 1 allergen.

Example 2

According to the invention up-dosing may be carried out in a fast way using the schedule described below:

Only two concentrations of the composition of the invention is required and the maintenance dose can be reached in 4 weeks with 1 injection every week, or in 2½ week with injection every 3-4 days. Up-dosing schedule:

TABLE 3

| Injection number | Vial | Injection volume in ml* | administered dose |
|---|---|---|---|
| 1 | Vial A | 0.5 | 300 SQ-E |
| 2 | 600 SQ-E/ml 22.6 µg Al/ml | 1 | 600 SQ-E |
| 3 | Vial B | 0.1 | 3000 SQ-E |
| 4 | 30.000 SQ-E/ml | 0.2 | 6000 SQ-E |
| 5 | 1.13 mg Al/ml | 0.5 | 15.000 SQ-E |

Injection intervals: Once every week or every 3-4 days
If interval exceeds 2-3 weeks: Repeat last dose
If interval exceeds 3-4 weeks: Reduce to half the previous dose
If interval→4 weeks: Restart with vial A
15.000 SQ-E corresponds to 0.6 to 22.5 µg of major allergen(s), 0.075 µg to 3.15 µg of clinically important major allergen, 1.5 µg to 3 µg group 5 allergen from grass or group 1 allergen from trees; or 0.75 µg to 2.25 µg mite group 1 allergen, about 0.55 µg olive group 1 allergen, about 0.9 µg parietaria group 1 allergen about 1.4 µg Artemisia group 1 allergen and about 0.075 µg *Alternaria* group 1 allergen.

Especially for grass allergy, up-dosing with 5 injections with one week between injections is safer than up-dosing with 3 injections with 1 day between each dose, and up-dosing in 5 steps with 3-4 days between the injections.

Example 3

The same up-dosing schedule as in example 2 with the sole exception that one injection is given every 3-14 days.

Example 4

According to a less preferred embodiment of the invention up-dosing may be carried out in a flexible and fast way using the schedule described below:
Only 2 concentrations of the formulation are required and the maintenance dose can be reached with 8 injections with one injection every 3-14 days.
Up-dosing schedule:

TABLE 4

| Injection number | Vial | Injection volume in ml* | administered dose |
|---|---|---|---|
| 1 | Vial A | 0.15 | 90 SQ-E |
| 2 | 600 SQ-E/ml | 0.5 | 300 SQ-E |
| 3 | 22.6 µg Al/ml | 1 | 600 SQ-E |
| 4 | Vial B | 0.05 | 1500 SQ-E |
| 5 | 30.000 SQ-E/ml | 0.1 | 3000 SQ-E |
| 6 | 1.13 mg Al/ml | 0.2 | 6000 SQ-E |
| 7 |  | 0.3 | 9000 SQ-E |
| 8 |  | 0.5 | 15.000 SQ-E |

Injection intervals: every 3-14 days
If interval exceeds 2-3 weeks: Repeat last dose
If interval exceeds 3-4 weeks: Reduce to half the previous dose
If interval→4 weeks: Restart with vial A
15.000 SQ-E corresponds to 0.6 to 22.5 µg of major allergen(s), 0.075 µg to 3.15 µg of clinically important major allergen, 1.5 µg to 3 µg group 5 allergen from grass or group 1 allergen from trees, or 0.75 µg to 2.25 µg mite group 1 allergen, about 0.55 µg olive group 1 allergen, about 0.9 µg parietaria group 1 allergen, about 1.4 µg Artemisia group 1 allergen and about 0.075 µg *Alternaria* group 1 allergen.

The invention claimed is:

1. A method for up-dosing in connection with allergy vaccination, comprising administering a composition comprising an allergen extract of a naturally occurring allergen adsorbed onto aluminium hydroxide as adjuvant, wherein said composition is either contained in one unit with one concentration of allergen or is contained in two or more separate units with different concentrations of allergen, characterized in that the administration is 4, 5, or 6 subcutaneous injections with increasing amount of allergen wherein the interval between the injections is ranging from 6 to 8 days and wherein the maximal dose of the up-dosing phase comprises aluminium hydroxide in an amount corresponding to 0.3 to 0.8 mg aluminium ion per dose and wherein the ratio of allergen to aluminium ion is the same throughout the up-dosing phase and the maintenance phase.

2. The method according to claim 1, wherein the compositions are administered as 5 subcutaneous injections with increasing amount of allergen.

3. The method according to claim 1, wherein said composition is contained in two units each containing a composition with different concentrations of allergen.

4. The method according to claim 1, wherein the interval between the injections is 7 days.

5. The method according to claim 1, wherein the maximum dose of the up-dosing phase contains 0.005 to 0.5 mg extract.

6. The method according to claim 1, wherein the maximum dose of the up-dosing phase contains 0.01 to 0.2 mg extract.

7. The method according to claim 1, wherein the amount of a single clinically important major allergen in the last injection of the up-dosing phase is 0.025 to 10.5 µg of clinically important major allergen.

8. The method according to claim 1, wherein the amount of a single clinically important major allergen in the last injection of the up-dosing phase is 0.05 µg to 4.2 µg of clinically important major allergen.

9. The method according to claim 1, wherein the amount of a single clinically important major allergen in the last injection of the up-dosing phase is 0.05 µg to 3.6 µg of clinically important major allergen.

10. The method according to claim 1, wherein the amount of a single clinically important major allergen in the last injection of the up-dosing phase is 0.075 µg to 3.15 µg of clinically important major allergen.

11. The method according to claim 1, wherein the naturally occurring allergen is a pollen allergen.

12. The method according to claim 1, wherein the naturally occurring allergen is a grass pollen allergen.

13. The method according to claim 1, wherein the naturally occurring allergen is a tree pollen allergen.

14. The method according to claim 1, wherein the naturally occurring allergen is a weed pollen allergen.

15. The method according to claim 1, wherein the naturally occurring allergen is a mite allergen.

16. The method according to claim 1, wherein the allergen extract is a grass allergen extract and the amount of group 5 allergen in the last injection of the up-dosing phase is 0.1 µg to 10 µg.

17. The method according to claim 1, wherein the allergen extract is a grass allergen extract and the amount of group 5 allergen in the last injection of the up-dosing phase is 0.5 µg to 6 µg.

18. The method according to claim 1, wherein the allergen extract is a grass allergen extract and the amount of group 5 allergen in the last injection of the up-dosing phase is 2.5 µg to 3.5 µg.

19. The method according to claim 1, wherein the allergen extract is a grass allergen extract and the amount of group 5 allergen in the last injection of the up-dosing phase is 1.5 µg to 3 µg.

20. The method according to claim 1, wherein the allergen extract is a tree allergen extract and the amount of group 1 allergen in the last injection of the up-dosing phase is 0.1 µg to 10 µg.

21. The method according to claim 1, wherein the allergen extract is a tree allergen extract and the amount of group 1 allergen in the last injection of the up-dosing phase is 0.5 µg to 6 µg.

22. The method according to claim 1, wherein the allergen extract is a tree allergen extract and the amount of group 1 allergen in the last injection of the up-dosing phase is 1 µg to 4 µg.

23. The method according to claim 1, wherein the allergen extract is a mite extract and the amount of group 1 allergen in the last injection of the up-dosing phase is 0.1 µg to 7.5 µg.

24. The method according to claim 1, wherein the allergen extract is a mite extract and the amount of group 1 allergen in the last injection of the up-dosing phase is 0.25 µg to 4.5 µg.

25. The method according to claim 1, wherein the allergen extract is a mite extract and the amount of group 1 allergen in the last injection of the up-dosing phase is 0.5 µg to 3 µg.

26. The method according to claim 1, wherein the interval between the number of up-dosing doses is 5 and the interval between injections is 7 days.

\* \* \* \* \*